(12) United States Patent
Rai (10) Patent No.: US 11,314,398 B2
(45) Date of Patent: Apr. 26, 2022

(54) METHOD AND SYSTEM FOR ENHANCED VISUALIZATION OF ULTRASOUND IMAGES BY PERFORMING PREDICTIVE IMAGE DEPTH SELECTION

(71) Applicant: GENERAL ELECTRIC COMPANY, Schenectady, NY (US)

(72) Inventor: Sushma Rai, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 675 days.

(21) Appl. No.: 15/704,924

(22) Filed: Sep. 14, 2017

(65) Prior Publication Data
US 2018/0164991 A1 Jun. 14, 2018

(30) Foreign Application Priority Data

Dec. 14, 2016 (IN) .............................. 201641042691

(51) Int. Cl.
| | |
|---|---|
| *G06F 3/04845* | (2022.01) |
| *G06F 3/04815* | (2022.01) |
| *G06F 3/0488* | (2022.01) |
| *G06F 3/04847* | (2022.01) |
| *G01S 15/89* | (2006.01) |

(Continued)

(52) U.S. Cl.
CPC .......... *G06F 3/04845* (2013.01); *A61B 8/465* (2013.01); *A61B 8/467* (2013.01); *A61B 8/54* (2013.01); *G01S 7/52063* (2013.01); *G01S 7/52073* (2013.01); *G01S 15/8913* (2013.01); *G06F 3/0488* (2013.01); *G06F 3/04815* (2013.01); *G06F 3/04847* (2013.01); *G06F 2203/04806* (2013.01); *G06T 3/0068* (2013.01); *G06T 3/20* (2013.01)

(58) Field of Classification Search
CPC .. A61B 8/00; A61B 8/52; A61B 8/483; A61B 8/465; A61B 8/467; A61B 8/54; G06F 3/0484; G06F 3/0488; G06F 3/04845; G06F 3/04815; G06F 3/04847; G06F 2203/04806; G01S 7/52063; G01S 7/52073; G01S 15/8913; G06T 3/0068; G06T 3/20

See application file for complete search history.

(56) References Cited

U.S. PATENT DOCUMENTS

| | | | | |
|---|---|---|---|---|
| 6,123,670 A | * | 9/2000 | Mo ........................ | A61B 8/469 600/447 |
| 2014/0044325 A1 | * | 2/2014 | Ma ......................... | G06T 19/00 382/128 |
| 2014/0300569 A1 | * | 10/2014 | Matsuki .................. | G06F 3/041 345/173 |

* cited by examiner

*Primary Examiner* — Quoc A Tran
(74) *Attorney, Agent, or Firm* — McAndrews, Held & Malloy, Ltd.; Jacob Groethe; David Bates (57) ABSTRACT

A system and method for predicting an ultrasound image depth selection is provided. The method may include presenting, at a display system, ultrasound image data acquired according to an initial depth setting. The method may include receiving a user input adjusting a zoom level of the ultrasound image data presented at the display system. The method may include processing the ultrasound image data presented at the display system to instantaneously and smoothly transition to the adjusted zoom level in response to the user input. The method may include receiving a user input selecting a selected zoom level of the ultrasound image data presented at the display system. The method may include determining a modified depth setting corresponding to the selected zoom level. The method may include acquiring updated ultrasound image data based on the modified depth setting for display at the display system.

20 Claims, 6 Drawing Sheets

(51) Int. Cl.
*A61B 8/00* (2006.01)
*G01S 7/52* (2006.01)
*G06T 3/20* (2006.01)
*G06T 3/00* (2006.01)
*G06F 17/00* (2019.01)

METHOD AND SYSTEM FOR ENHANCED VISUALIZATION OF ULTRASOUND IMAGES BY PERFORMING PREDICTIVE IMAGE DEPTH SELECTION

CROSS-REFERENCE TO RELATED APPLICATIONS/INCORPORATION BY REFERENCE

The present application claims priority to Indian Patent Application No. 201641042691, filed Dec. 14, 2016. The content of the above-identified application is hereby incorporated herein by reference in its entirety.

FIELD

Certain embodiments relate to ultrasound imaging. More specifically, certain embodiments relate to a method and system for enhanced visualization of ultrasound images by predicting an image depth selection. The method and system may be operable to acquire and display first ultrasound scan data, instantaneously and smoothly display zoom level adjustments of the first ultrasound scan data according to a user input, and acquire and display second ultrasound scan data according to an updated depth setting corresponding with the user selected zoom level.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Ultrasound imaging systems perform scans based on operating parameters, such as depth, gain, focus, frequency, and the like. The depth of an ultrasound image scan is typically determined by a trial and error approach. For example, an ultrasound operator may perform multiple ultrasound scans at different depths to determine a desired depth for the examination.

Figure 1:
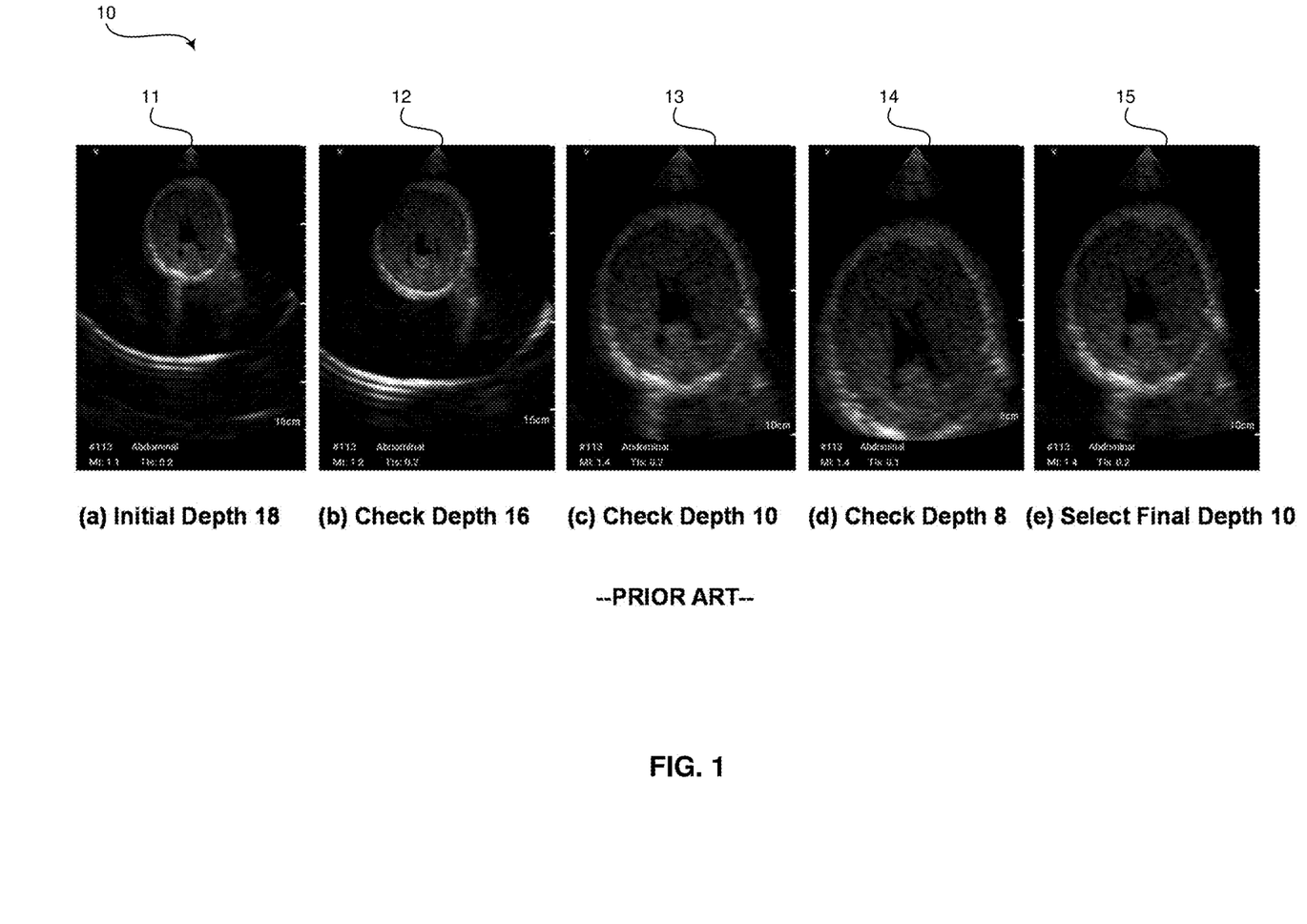
FIG. 1 illustrates a series of exemplary ultrasound images acquired at steps in an exemplary conventional method for choosing a desired ultrasound image depth, as known in the art.

FIG. 1 illustrates a series of exemplary ultrasound images 10 acquired at steps (a)-(e) in an exemplary conventional method for choosing a desired ultrasound image depth, as known in the art. At step (a), an operator uses an ultrasound system to perform a scan at an initial depth, which may be a default or operator-selected initial depth. For example, the operator may perform a scan at an initial depth of 18 centimeters. The image data 11 acquired according to the initial depth may be displayed at a display system.

At step (b), the operator modifies the depth setting and uses the ultrasound system to perform a second scan at the modified depth. For example, the operator may adjust a rotary knob or slider user input module to adjust the depth from 18 centimeters to 16 centimeters and then initiate the second scan. The image data 12 from the second scan may be displayed at the display system such that the operator can determine whether the current depth setting covers the entire area of interest in the view plane.

At steps (c) and (d), the ultrasound operator may continue to make depth setting adjustments to acquire and display images 13, 14 for review by the operator. Once the operator determines the desired depth setting, the operator may perform the ultrasound examination at step (e) to acquire and display images 15 based on the selected depth setting. Conventional ultrasound systems typically take about 3-4 seconds to acquire and display ultrasound data at each modified depth. Accordingly, the conventional trial and error approach for determining a desired depth for an ultrasound examination can be an inefficient, time-consuming process for an ultrasound operator.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for enhanced visualization of ultrasound images by predicting an image depth selection, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for providing enhanced visualization of ultrasound images by predicting an image depth selection. Various embodiments have the technical effect of predicting an image depth selection based on a selected zoom level adjustment in ultrasound image data. For example, various aspects have the technical effect of instantaneously and smoothly displaying zoom level adjustments of first acquired and displayed ultrasound scan data according to a user input. Moreover, certain embodiments have the technical effect of acquiring and displaying second ultrasound scan data according to an updated depth setting corresponding with the user selected zoom level.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode, and/or sub-modes of B-mode and/or CF such as Shear Wave Elasticity Imaging (SWEI), TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 2.

Figure 2:
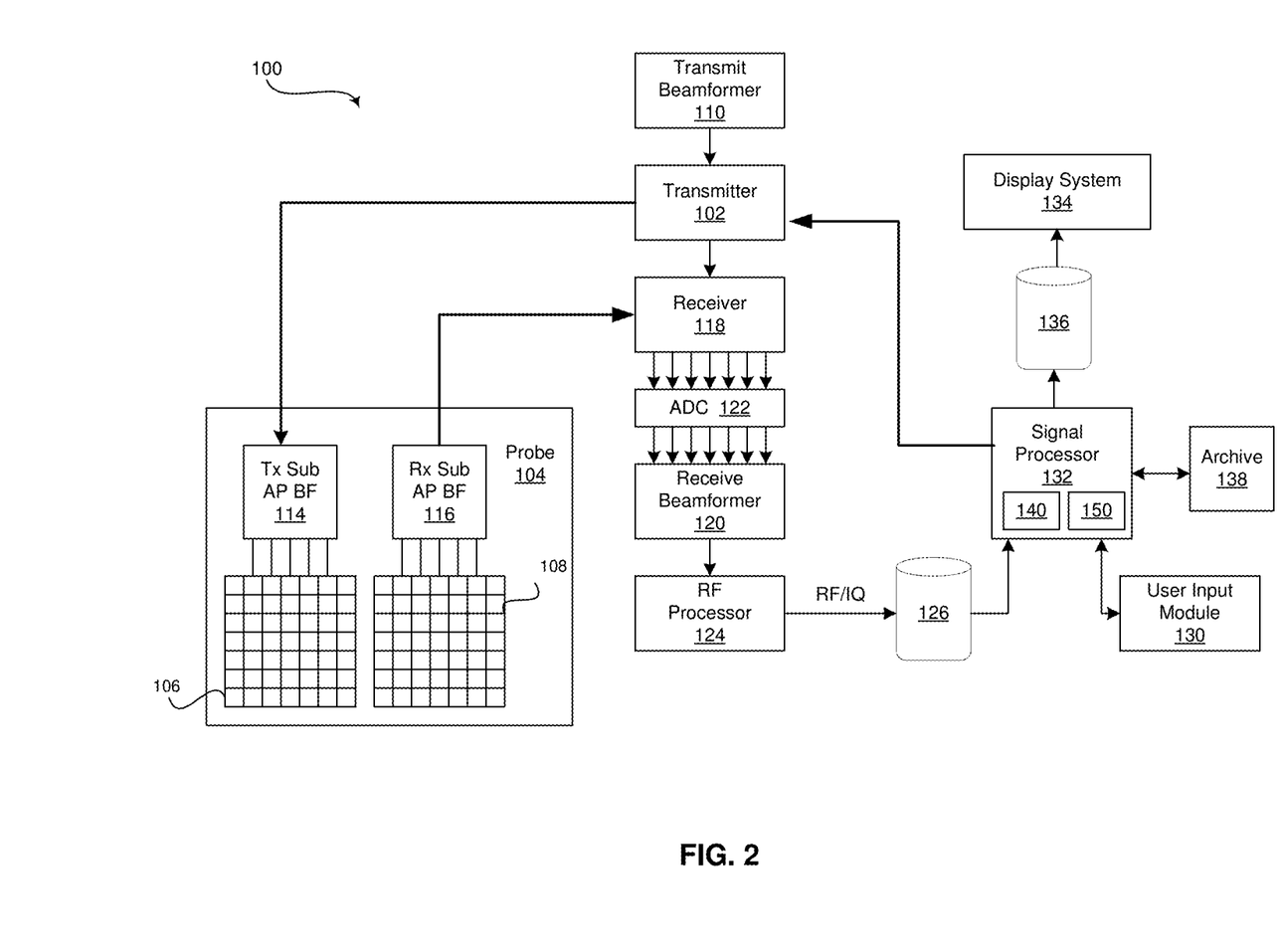
FIG. 2 is a block diagram of an exemplary ultrasound system that is operable to provide enhanced visualization of ultrasound images by predicting an image depth selection, in accordance with various embodiments.

FIG. 2 is a block diagram of an exemplary ultrasound system 100 that is operable to provide enhanced visualization of ultrasound images by predicting an image depth selection, in accordance with various embodiments. Referring to FIG. 2, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the disclosure is not limited in this regard. Accordingly, in some embodiments, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, surgical instrument data, scan parameters, settings, configuration parameters, render settings, change scan mode, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the display system 134, and/or the archive 138. The user input module 130 may include button(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display. In various embodiments, an ultrasound image presented at the display system 134 may be manipulated to zoom in and/or out in response to a directive received via the user input module 130.

The signal processor 132 may comprise suitable logic, circuitry, interfaces and/or code that may be operable to process ultrasound scan data (i.e., RF signal data or IQ data pairs) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. The processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise an image zoom module 140 and a depth setting prediction module 150.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image zoom module 140 that comprises suitable logic, circuitry, interfaces and/or code that may be operable to instantaneously modify the presentation of acquired ultrasound image data in response to user instructions provided at the user input module 130. For example, the image zoom module 140 may receive a user input adjusting a zoom level of an ultrasound image presented at the display system 13. The image zoom module 140 may instantaneously and smoothly zoom in and/or out of the displayed ultrasound image in response to the user input. In various embodiments, the image zoom module 140 may pan or otherwise shift the image data synchronously with the zoom operation such that the top of the displayed image is continuously aligned with the top of the image display as described below with reference to FIGS. 4-5. In an exemplary embodiment, the ultrasound operator can select a desired scaling of the area of interest in the view plane of the current ultrasound image that may be applied by the depth setting module 150 to predict and apply an image depth selection as described below.

Figure 3:
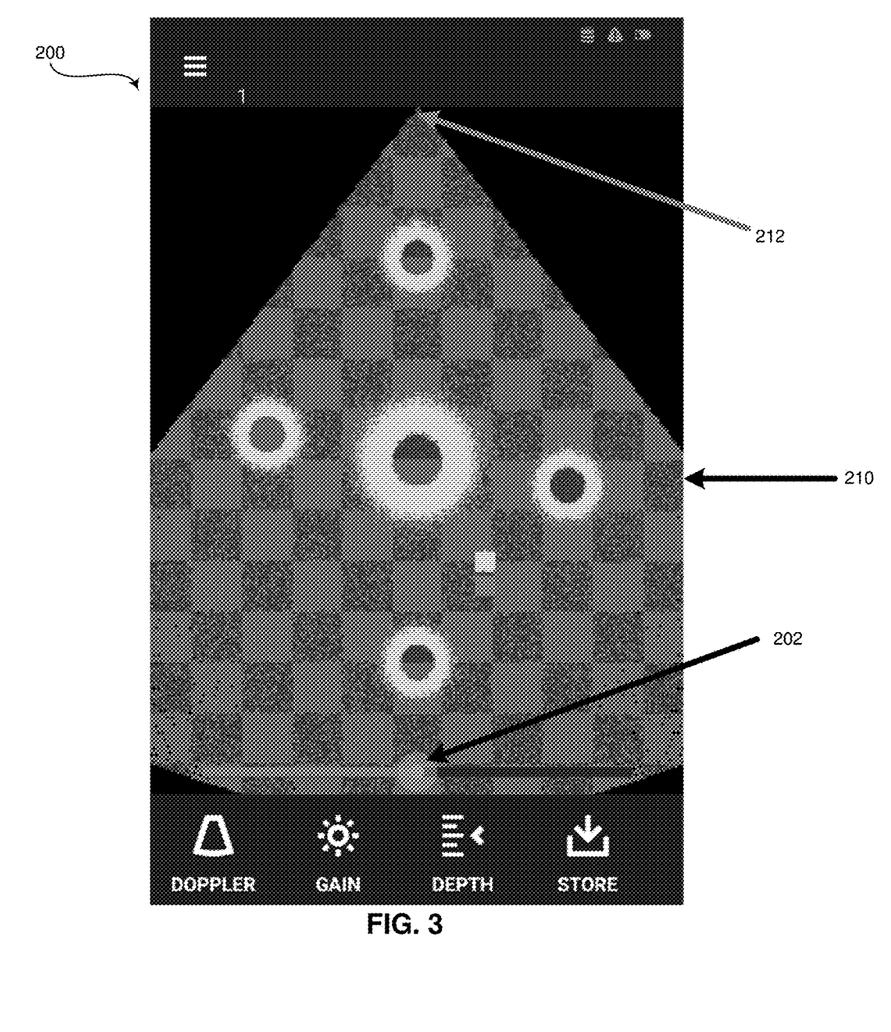
FIG. 3 is a screenshot of an exemplary image display including acquired ultrasound image data and an exemplary image depth adjustment user interface, in accordance with exemplary embodiments.

FIG. 3 is a screenshot of an exemplary image display 200 including acquired ultrasound image data 210 and an exemplary image depth adjustment user interface 202, in accordance with exemplary embodiments. Referring to FIG. 3, an ultrasound operator may manipulate the image depth adjustment user interface 202, such as with a touch input at a touchscreen user input module 130 or with any suitable input via any suitable input module 130. For example, increasing the zoom via the image depth adjustment user interface 202 may cause the image data 210 to zoom in and decreasing the zoom may cause the image data 210 to zoom out.

Figure 4:
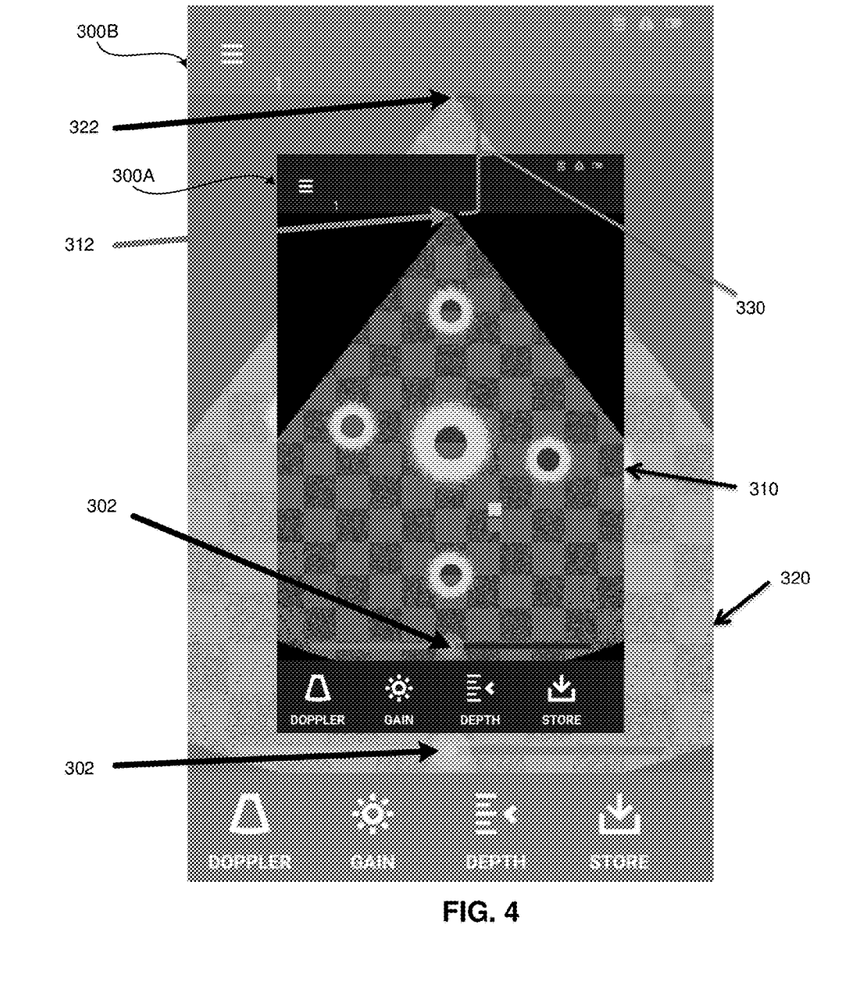
FIG. 4 illustrates screenshots of exemplary image displays each including acquired ultrasound image data presented at different zoom levels, in accordance with exemplary embodiments.

In various embodiments, the image zoom module 140 may be configured to shift the top 212 of the image data 210 down in a zoomed in image and/or shift the top 212 of the image data 210 up in a zoomed out image, for example, if the zoom operation is implemented relative to a center of the image 210. FIG. 4 illustrates screenshots of exemplary image displays 300A, 300B each including acquired ultrasound image data 310, 320 presented at different zoom levels, in accordance with exemplary embodiments. Referring to FIG. 4, the ultrasound image data 310 in the first image display 300A may be presented at a lesser zoom level than the same ultrasound image data 320 presented in the second image display 300B. The image zoom module 140 may be configured to shift 330 the top 322 of the image data 320 down if performing a zooming in operation. As an example, if the image data 310 in the first image display 300A is scaled by 150% relative to the center of the image data 320 in the second image display 300B, the image zoom module 140 may pan down to align the top 322 of the zoomed in image 320 to the top of the second image display 300B. In various embodiments, the amount of down shift may be calculated by the image zoom module 140 based on the following:

$$\text{Down Shift} = \left(\frac{\text{Image Display Zoom \%}}{100} - 1\right) \times \frac{\text{Image Display Vertical Size}}{2}$$

For example, if the first image data 310 is scaled by 150% to present the second image data 320 in a display system 134 having a 20 inch vertical viewing area, the top 322 of the second image data 320 may be shifted 330 down 5 inches by the image zoom module 140. The image zoom module 140 may perform the down shift operation synchronously with the zooming in operation.

The image zoom module 140 may be configured to shift 330 the top 322 of the image data 320 up if performing a zooming out operation. For example, if the image data 320 in the second image display 300B is scaled by 60% relative to the center of the image data 310 in the first image display 300A, the image zoom module 140 may pan up to align the top 312 of the zoomed out image 310 to the top of the first image display 300A. In various embodiments, the amount of up shift may be calculated by the image zoom module 140 based on the following:

$$\text{Up Shift} = \left(1 - \frac{\text{Image Display Zoom \%}}{100}\right) \times \frac{\text{Image Display Vertical Size}}{2}$$

For example, if the second image data 320 is scaled by 60% to present the first image data 310 in a display system 134 having a 20 inch vertical viewing area, the top 312 of the first image data 310 may be shifted 330 up 4 inches by the image zoom module 140. In certain embodiments, blank image data (not shown) may be present at the bottom and/or side edges of the zoomed out image data 310 if, for example, the zoom out operation is carried out with respect to the original non-zoomed ultrasound image data. The image zoom module 140 may perform the up shift operation simultaneously with the zooming out operation.

Figure 5:
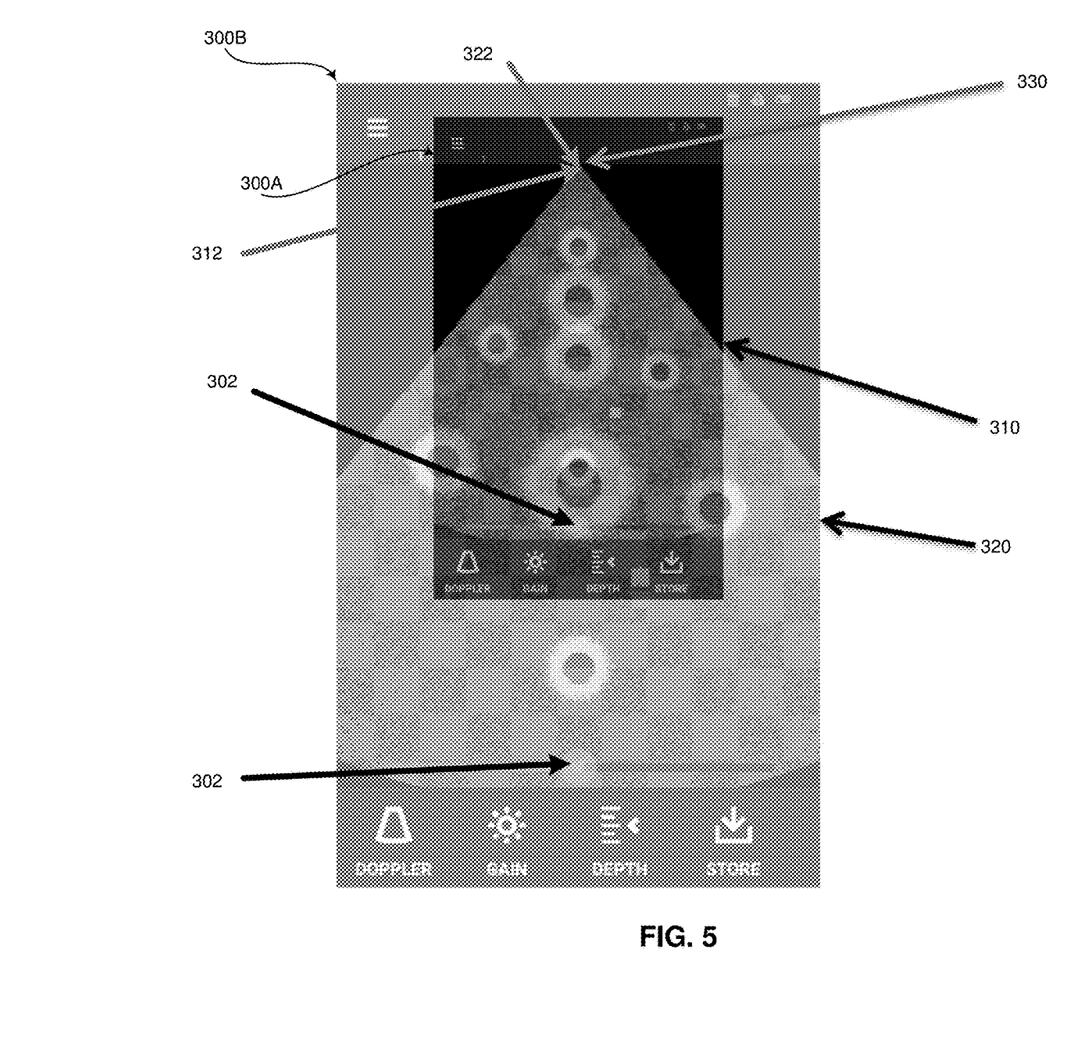
FIG. 5 illustrates screenshots of exemplary image displays each including acquired ultrasound image data presented in alignment at different zoom levels, in accordance with exemplary embodiments.

FIG. 5 illustrates screenshots of exemplary image displays 300A, 300B each including acquired ultrasound image data 310, 320 presented in alignment 330 at different zoom levels, in accordance with exemplary embodiments. Referring to FIG. 5, the first 300A and second 300B image displays each comprise ultrasound image data 310, 320 and an image depth adjustment user interface 202. The image depth adjustment user interface 202 may be configured to receive an input via a user input module 130 to manipulate the scale of the ultrasound image data 310, 320. The image zoom module 140 may be configured to present the top 312, 322 of the scaled image data 310, 320 aligned 330 with the top of the image display 300A, 300B.

Referring again to FIG. 2, the signal processor 132 may include a depth setting module 150 that comprises suitable logic, circuitry, interfaces and/or code that may be operable to predict an image depth selection. The depth setting module 150 may predict the depth selection based on the zoom level selected via the image zoom module 140. The predicted depth selection may be applied by the depth setting module 150 to the ultrasound system 100 to perform a subsequent ultrasound image scan. In various embodiments, the predicted depth selection may be calculated by the depth setting module 150 based on the following:

$$\text{Predicted Depth Selection} = \left(\frac{\text{Depth of Current Ultrasound Image}}{\text{Image Display Zoom \%}}\right) \times 100$$

For example, if an ultrasound scan is performed with a depth setting of 12 cm and the image zoom module 140 sets the image display zoom % of the ultrasound scan data to 60% based on a user input, the depth setting module 150 may predict a depth selection of 20 cm. As another example, if an ultrasound scan is performed with a depth setting of 12 cm and an input is provided modifying the image display zoom % of the ultrasound scan data to 150%, the depth setting module 150 may predict a depth selection of 8 cm.

Figure 6:
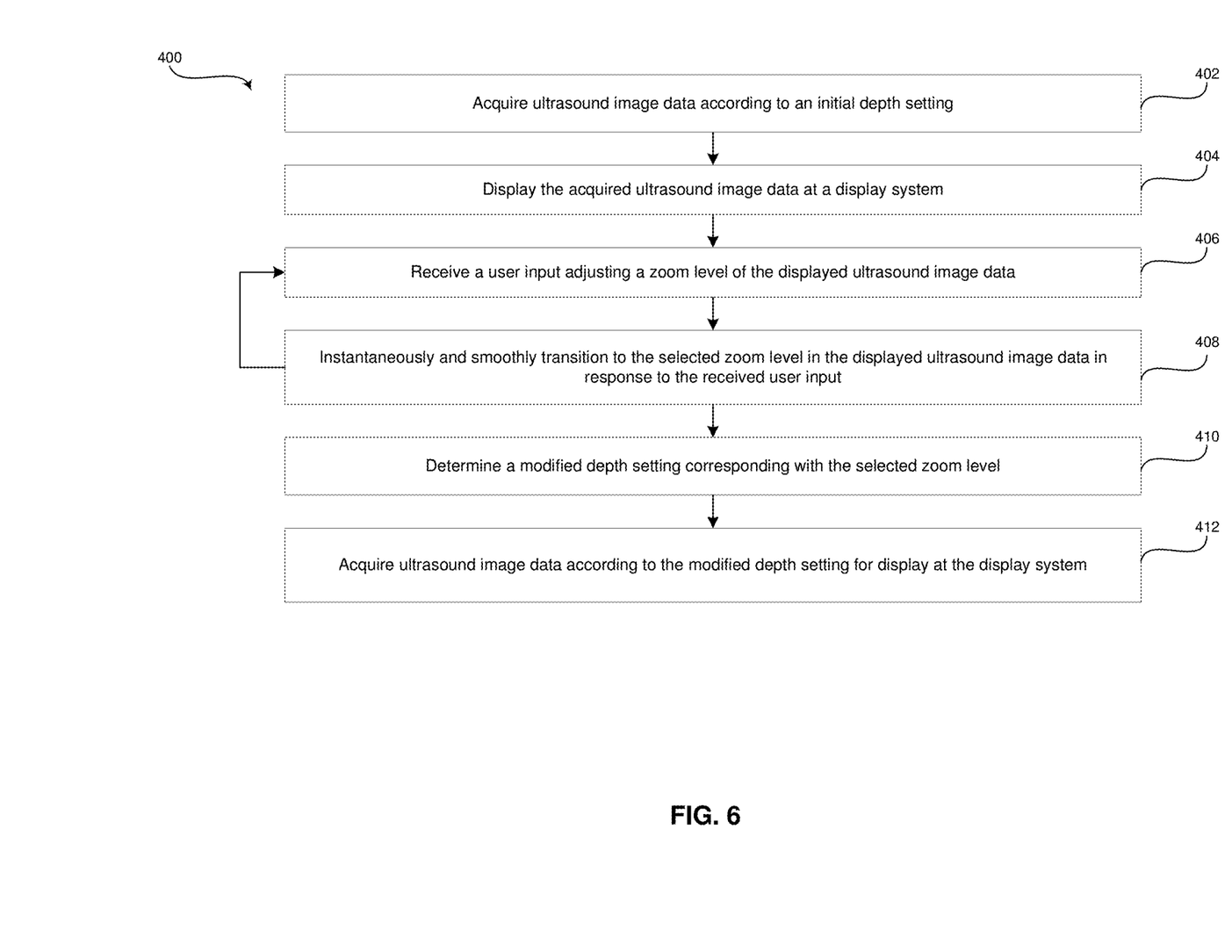
FIG. 6 is a flow chart illustrating exemplary steps that may be utilized for providing enhanced visualization of ultrasound images by predicting an image depth selection, in accordance with various embodiments.

FIG. 6 is a flow chart 400 illustrating exemplary steps 402-412 that may be utilized for providing enhanced visualization of ultrasound images by predicting an image depth selection, in accordance with various embodiments. Referring to FIG. 4, there is shown a flow chart 400 comprising exemplary steps 402 through 412. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, an ultrasound system 100 may acquire ultrasound image data according to an initial depth setting. For example, the ultrasound system 100 may acquire image data based on operating parameters, such as depth, gain, and the like. The operating parameters may be default parameters, parameters associated with a particular selected imaging mode, or user-defined parameters, among other things.

At step 404, a signal processor 132 of the ultrasound system 100 may display the acquired ultrasound image data at a display system 134. For example, the signal processor 132 may generate ultrasound images for presentation on a display system 134 from the data acquired by the ultrasound system 100 at the initial depth setting.

At step 406, the signal processor 132 may receive, via a user input module 130, a user input to adjust a zoom level of the displayed ultrasound image data. For example, the user input module 130 may be a touchscreen user input device or any suitable user input device. The user input manipulate an image depth adjustment user interface 202, 302 presented at the user input module 130 and/or display 134. The image depth adjustment user interface 202, 302 may be manipulated, for example, to provide an instruction to zoom in and/or zoom out of the displayed ultrasound image 210, 310, 320. The instruction may be provided to an image zoom module 140 of the signal processor 132. As an example, an ultrasound operator may drag a finger across a touchscreen user input module 130 to slide the image depth adjustment user interface 202, 302. The sliding of the image depth adjustment user interface 202, 302 may correspond with a zoom operation, such as zooming in if sliding in a first direction and zooming out if sliding in a second direction opposite the first direction. In various embodiments, the operator may select a zoom level by removing the finger from the touchscreen user input module 130 once the ultrasound image data 210, 310, 320 presented at the display system 134 is at a scale desired by the operator. Additionally and/or alternatively, a button, knob, slider, or any suitable user input module 130 may be utilized to adjust and select a desired zoom level.

At step 408, the signal processor 132 may instantaneously and smoothly transition to the selected zoom level in the displayed ultrasound image data in response to the received user input. For example, the image zoom module 140 of the signal processor 132 may smoothly scale the displayed ultrasound image 210, 310, 320 as the zoom level adjustments are received such that the scaling of the displayed ultrasound image 210, 310, 320 is updated in substantially real-time. In various embodiments, the image zoom module 140 may pan or otherwise shift the image data 210, 310, 320 synchronously with the zoom operation such that the top 212, 312, 322 of the displayed image 210, 310, 320 is continuously aligned with the top of the image display 200, 300B, 300B in the display system 134. As an example, in response to the ultrasound operator dragging a finger across a touchscreen user input module 130 to slide the image depth adjustment user interface 202, 302, the image zoom module 140 may smoothly scale and pan the ultrasound image data 210, 310, 320 presented at the display system 134 in substantially real-time as the finger of the operator manipulates the image depth adjustment user interface 202, 302.

At step 410, the signal processor 132 may determine a modified depth setting corresponding with the selected zoom level. For example, a depth setting module 150 of the signal processor 132 may calculate the modified depth setting based on the zoom level selected at step 406. In various embodiments, the available zoom levels may each be associated with a depth setting. The depth setting module 150 may apply the modified depth setting operating parameter to the ultrasound system 100.

At step 412, the ultrasound system 100 may acquire ultrasound image data according to the modified depth setting for display at the display system 134. For example, the ultrasound system 100 may perform a scan to acquire ultrasound image data in response to the application of the modified depth setting by the depth setting module 150. The ultrasound image data acquired according to the modified depth setting may be processed by the signal processor 132 and presented at the display system 134.

Aspects of the present disclosure provide a method 400 and system 100 for providing enhanced visualization of ultrasound images 210, 310, 320 by predicting an image depth selection. In accordance with various embodiments, the method 400 may comprise presenting 404, at a display system 134, ultrasound image data 210, 310, 320 acquired according to an initial depth setting. The method 400 may comprise receiving 406, via a user input module 130, a user input adjusting a zoom level of the ultrasound image data 210, 310, 320 presented at the display system 134. The method 400 may comprise processing 408, by a processor 132, 140, the ultrasound image data 210, 310, 320 presented at the display system 134 to instantaneously and smoothly transition to the adjusted zoom level in response to the user input. The method 400 may comprise receiving 406, via the user input module 130, a user input selecting a selected zoom level of the ultrasound image data 210, 310, 320 presented at the display system 134. The method 400 may comprise determining 410, by the processor 132, 150, a modified depth setting corresponding to the selected zoom level. The method 400 may comprise acquiring 412 updated ultrasound image data 210, 310, 320 based on the modified depth setting for display at the display system 134.

In various embodiments, the method 400 comprises acquiring 402, 412, by an ultrasound device 100, the ultrasound image data 210, 310, 320 and the updated ultrasound image data 210, 310, 320. In a representative embodiment, the user input module 130 is a touchscreen user input module. In certain embodiments, the user input selecting a selected zoom level is a removal of a touch input from the touchscreen user input module 130. In various embodiments, the modified depth setting is determined based on:

$$\text{Predicted Depth Selection} = \left(\frac{\text{Depth of Current Ultrasound Image}}{\text{Image Display Zoom \%}}\right) \times 100,$$

wherein the Predicted Depth Selection is the modified depth setting, the Depth of Current Ultrasound Image is the initial depth setting, and the Image Display Zoom % is the selected zoom level.

In a representative embodiment, the ultrasound image data 210, 310, 320 comprises a top portion 212, 312, 322 aligned 330 with a top of a display area 200, 300A, 300B of the display system 134. The transition to the adjusted zoom level may comprise scaling the ultrasound image data 210, 310, 320 relative to a center of the ultrasound image data 210, 310, 320. The transition to the adjusted zoom level may comprise shifting the ultrasound data 210, 310, 320 to re-align 330 the top portion 212, 312, 322 of the scaled ultrasound image data 210, 310, 320 with the top of the display area 200, 300A, 300B of the display system 134.

In various embodiments, if the adjusted zoom level corresponds with a zoom in operation, an amount of the shifting the ultrasound data 210, 310, 320 is determined based on:

$$\text{Down Shift} = \left(\frac{\text{Image Display Zoom \%}}{100} - 1\right) \times \frac{\text{Image Display Vertical Size}}{2},$$

wherein the Down Shift corresponds to the amount of shift 330 provided in a downward direction from the top of the display area 200, 300A, 300B of the display system 134, the Image Display Zoom % corresponds to the selected zoom level, and the Image Display Vertical Size corresponds to a vertical size of the display area 200, 300A, 300B of the display system 134.

In certain embodiments, if the adjusted zoom level corresponds with a zoom out operation, an amount of the shifting the ultrasound data 210, 310, 320 is determined based on:

$$\text{Up Shift} = \left(1 - \frac{\text{Image Display Zoom \%}}{100}\right) \times \frac{\text{Image Display Vertical Size}}{2},$$

wherein the Up Shift corresponds to the amount of shift 330 provided in an upward direction from the top of the display area 200, 300A, 300B of the display system 134, the Image Display Zoom % corresponds to the selected zoom level, and the Image Display Vertical Size corresponds to a vertical size of the display area 200, 300A, 300B of the display system 134.

Various embodiments provide a system 100 for providing enhanced visualization of ultrasound images 210, 310, 320 by predicting an image depth selection. The system 100 may comprise a display system 134 configured to present ultrasound image data 210, 310, 320 acquired according to an initial depth setting. The system 100 may comprise a user input module 130 configured to receive a user input adjusting a zoom level of the ultrasound image data 210, 310, 320 presented at the display system 134. The user input module 130 may be configured to receive a user input selecting a selected zoom level of the ultrasound image data 210, 310, 320 presented at the display system 134. The system 100 may comprise a processor 132, 140 configured to process the ultrasound image data 210, 310, 320 presented at the display system 134 to instantaneously and smoothly transition to the adjusted zoom level in response to the user input. The processor 132, 150 may be configured to determine a modified depth setting corresponding to the selected zoom level. The system 100 may comprise an ultrasound device 100 configured to acquire updated ultrasound image data 210, 310, 320 based on the modified depth setting for display at the display system 134.

In certain embodiments, the ultrasound device 100 is configured to acquire the ultrasound image data 210, 310, 320 acquired according to the initial depth setting. In a representative embodiment, the user input module 130 is a touchscreen user input module. In various embodiments, the user input selecting a selected zoom level is a removal of a touch input from the touchscreen user input module 130. In certain embodiments, the processor 132, 150 is configured to determine the modified depth setting based on:

$$\text{Predicted Depth Selection} = \left(\frac{\text{Depth of Current Ultrasound Image}}{\text{Image Display Zoom \%}}\right) \times 100,$$

wherein the Predicted Depth Selection is the modified depth setting, the Depth of Current Ultrasound Image is the initial depth setting, and the Image Display Zoom % is the selected zoom level.

In a representative embodiment, the ultrasound image data 210, 310, 320 comprises a top portion 212, 312, 322 aligned 330 with a top of a display area 200, 300A, 300B of the display system 134. The processor 132, 140 is configured to transition to the adjusted zoom level by scaling the ultrasound image data 210, 310, 320 relative to a center of the ultrasound image data 210, 310, 320. The processor is configured to transition to the adjusted zoom level by shifting the ultrasound data 210, 310, 320 to re-align the top portion 212, 312, 322 of the scaled ultrasound image data 210, 310, 320 with the top of the display area 200, 300A, 300B of the display system 134.

In certain embodiments, if the adjusted zoom level corresponds with a zoom in operation, the processor 132, 140 is configured to shift the ultrasound data 210, 310, 320 an amount based on:

$$\text{Down Shift} = \left(\frac{\text{Image Display Zoom \%}}{100} - 1\right) \times \frac{\text{Image Display Vertical Size}}{2},$$

wherein the Down Shift corresponds to the amount of shift provided in a downward direction from the top of the display area 200, 300A, 300B of the display system 134, the Image Display Zoom % corresponds to the selected zoom level, and the Image Display Vertical Size corresponds to a vertical size of the display area 200, 300A, 300B of the display system 134.

In a representative embodiment, if the adjusted zoom level corresponds with a zoom out operation, the processor 132, 140 is configured to shift the ultrasound data an amount based on:

$$\text{Up Shift} = \left(1 - \frac{\text{Image Display Zoom \%}}{100}\right) \times \frac{\text{Image Display Vertical Size}}{2},$$

wherein the Up Shift corresponds to the amount of shift provided in an upward direction from the top of the display area 200, 300A, 300B of the display system 134, the Image Display Zoom % corresponds to the selected zoom level, and the Image Display Vertical Size corresponds to a vertical size of the display area 200, 300A, 300B of the display system 134.

Certain embodiments provide a non-transitory computer readable medium having stored thereon, a computer program having at least one code section. The at least one code section is executable by a machine for causing the machine to perform steps. The steps 400 may include presenting 404 ultrasound image data 210, 310, 320 acquired according to an initial depth setting. The steps 400 may include receiving 406 a user input adjusting a zoom level of the presented ultrasound image data 210, 310, 320. The steps 400 may include processing 408 the presented ultrasound image data 210, 310, 320 to instantaneously and smoothly transition to the adjusted zoom level in response to the user input. The steps 400 may include receiving 406 a user input selecting a selected zoom level of the presented ultrasound image data 210, 310, 320. The steps 400 may include determining 410 a modified depth setting corresponding to the selected zoom level. The steps 400 may include acquiring 412 updated ultrasound image data 210, 310, 320 based on the modified depth setting.

In various embodiments, the steps 400 may include presenting 412 the updated ultrasound image data 210, 310, 320 acquired based on the modified depth setting. In a representative embodiment, the modified depth setting may be determined based on:

$$\text{Predicted Depth Selection} = \left(\frac{\text{Depth of Current Ultrasound Image}}{\text{Image Display Zoom \%}}\right) \times 100,$$

wherein the Predicted Depth Selection is the modified depth setting, the Depth of Current Ultrasound Image is the initial depth setting, and the Image Display Zoom % is the selected zoom level. In certain embodiments, the ultrasound image data 210, 310, 320 comprises a top portion 212, 312, 322 aligned 330 with a top of a display area 200, 300A, 300B. The transition to the adjusted zoom level may comprise scaling the ultrasound image data 210, 310, 320 relative to a center of the ultrasound image data 210, 310, 320. The transition to the adjusted zoom level may comprise shifting the ultrasound data 210, 310, 320 to re-align 330 the top portion 212, 312, 322 of the scaled ultrasound image data 210, 310, 320 with the top of the display area 200, 300A, 300B.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing enhanced visualization of ultrasound images by predicting an image depth selection.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
presenting, at a display system, ultrasound image data acquired according to an initial depth setting;
receiving, via a user input module, a user input adjusting a zoom level of the ultrasound image data presented at the display system;
processing, by a processor, the ultrasound image data presented at the display system to instantaneously and smoothly transition to the adjusted zoom level in response to the user input;
receiving, via the user input module, a user input selecting a selected zoom level of the ultrasound image data presented at the display system;
determining, by the processor, a modified depth setting corresponding to the selected zoom level; and
acquiring updated ultrasound image data based on the modified depth setting for display at the display system.

2. The method according to claim 1, comprising acquiring, by an ultrasound device, the ultrasound image data and the updated ultrasound image data.

3. The method according to claim 1, wherein the user input module is a touchscreen user input module.

4. The method according to claim 3, wherein the user input selecting a selected zoom level is a removal of a touch input from the touchscreen user input module.

5. The method according to claim 1, wherein the modified depth setting is determined based on:

$$\text{Predicted Depth Selection} = \left(\frac{\text{Depth of Current Ultrasound Image}}{\text{Image Display Zoom \%}}\right) \times 100,$$

wherein the Predicted Depth Selection is the modified depth setting, the Depth of Current Ultrasound Image is the initial depth setting, and the Image Display Zoom % is the selected zoom level.

6. The method according to claim 1, wherein the ultrasound image data comprises a top portion aligned with a top of a display area of the display system, and wherein the transition to the adjusted zoom level comprises:
scaling the ultrasound image data relative to a center of the ultrasound image data, and
shifting the ultrasound data to re-align the top portion of the scaled ultrasound image data with the top of the display area of the display system.

7. The method according to claim 6, wherein if the adjusted zoom level corresponds with a zoom in operation, an amount of the shifting the ultrasound data is determined based on:

$$\text{Down Shift} = \left(\frac{\text{Image Display Zoom \%}}{100} - 1\right) \times \frac{\text{Image Display Vertical Size}}{2},$$

wherein the Down Shift corresponds to the amount of shift provided in a downward direction from the top of the display area of the display system, the Image Display Zoom % corresponds to the selected zoom level, and the Image Display Vertical Size corresponds to a vertical size of the display area of the display system.

8. The method according to claim 6, wherein if the adjusted zoom level corresponds with a zoom out operation, an amount of the shifting the ultrasound data is determined based on:

$$\text{Up Shift} = \left(1 - \frac{\text{Image Display Zoom \%}}{100}\right) \times \frac{\text{Image Display Vertical Size}}{2},$$

wherein the Up Shift corresponds to the amount of shift provided in an upward direction from the top of the display area of the display system, the Image Display Zoom % corresponds to the selected zoom level, and the Image Display Vertical Size corresponds to a vertical size of the display area of the display system.

9. A system comprising:
a display system configured to present ultrasound image data acquired according to an initial depth setting;
a user input module configured to:
receive a user input adjusting a zoom level of the ultrasound image data presented at the display system, and
receive a user input selecting a selected zoom level of the ultrasound image data presented at the display system;

a processor configured to:
: process the ultrasound image data presented at the display system to instantaneously and smoothly transition to the adjusted zoom level in response to the user input, and
: determine a modified depth setting corresponding to the selected zoom level; and an ultrasound device configured to acquire updated ultrasound image data based on the modified depth setting for display at the display system.

10. The system according to claim 9, wherein the ultrasound device is configured to acquire the ultrasound image data acquired according to the initial depth setting.

11. The system according to claim 9, wherein the user input module is a touchscreen user input module.

12. The system according to claim 11, wherein the user input selecting a selected zoom level is a removal of a touch input from the touchscreen user input module.

13. The system according to claim 9, wherein the processor is configured to determine the modified depth setting based on:

$$\text{Predicted Depth Selection} = \left(\frac{\text{Depth of Current Ultrasound Image}}{\text{Image Display Zoom \%}}\right) \times 100,$$

wherein the Predicted Depth Selection is the modified depth setting, the Depth of Current Ultrasound Image is the initial depth setting, and the Image Display Zoom % is the selected zoom level.

14. The system according to claim 9, wherein the ultrasound image data comprises a top portion aligned with a top of a display area of the display system, and wherein the processor is configured to transition to the adjusted zoom level by:
: scaling the ultrasound image data relative to a center of the ultrasound image data, and
: shifting the ultrasound data to re-align the top portion of the scaled ultrasound image data with the top of the display area of the display system.

15. The system according to claim 14, wherein if the adjusted zoom level corresponds with a zoom in operation, the processor is configured to shift the ultrasound data an amount based on:

$$\text{Down Shift} = \left(\frac{\text{Image Display Zoom \%}}{100} - 1\right) \times \frac{\text{Image Display Vertical Size}}{2},$$

wherein the Down Shift corresponds to the amount of shift provided in a downward direction from the top of the display area of the display system, the Image Display Zoom % corresponds to the selected zoom level, and the Image Display Vertical Size corresponds to a vertical size of the display area of the display system.

16. The system according to claim 14, wherein if the adjusted zoom level corresponds with a zoom out operation, the processor is configured to shift the ultrasound data an amount based on:

$$\text{Up Shift} = \left(1 - \frac{\text{Image Display Zoom \%}}{100}\right) \times \frac{\text{Image Display Vertical Size}}{2},$$

wherein the Up Shift corresponds to the amount of shift provided in an upward direction from the top of the display area of the display system, the Image Display Zoom % corresponds to the selected zoom level, and the Image Display Vertical Size corresponds to a vertical size of the display area of the display system.

17. A non-transitory computer readable medium having stored thereon, a computer program having at least one code section, the at least one code section being executable by a machine for causing the machine to perform steps comprising:
: presenting ultrasound image data acquired according to an initial depth setting;
: receiving a user input adjusting a zoom level of the presented ultrasound image data;
: processing the presented ultrasound image data to instantaneously and smoothly transition to the adjusted zoom level in response to the user input;
: receiving a user input selecting a selected zoom level of the presented ultrasound image data;
: determining a modified depth setting corresponding to the selected zoom level; and
: acquiring updated ultrasound image data based on the modified depth setting.

18. The non-transitory computer readable medium according to claim 17, comprising presenting the updated ultrasound image data acquired based on the modified depth setting.

19. The non-transitory computer readable medium according to claim 17, wherein the modified depth setting is determined based on:

$$\text{Predicted Depth Selection} = \left(\frac{\text{Depth of Current Ultrasound Image}}{\text{Image Display Zoom \%}}\right) \times 100,$$

wherein the Predicted Depth Selection is the modified depth setting, the Depth of Current Ultrasound Image is the initial depth setting, and the Image Display Zoom % is the selected zoom level.

20. The non-transitory computer readable medium according to claim 17, wherein the ultrasound image data comprises a top portion aligned with a top of a display area, and wherein the transition to the adjusted zoom level comprises:
: scaling the ultrasound image data relative to a center of the ultrasound image data, and
: shifting the ultrasound data to re-align the top portion of the scaled ultrasound image data with the top of the display area.

* * * * *